United States Patent [19]

McPhee

[11] 4,354,492
[45] Oct. 19, 1982

[54] MEDICAL ADMINISTRATION SET WITH BACKFLOW CHECK VALVE

[75] Inventor: Charles J. McPhee, Huntington Beach, Calif.

[73] Assignee: American Hospital Supply Corporation, Evanston, Ill.

[21] Appl. No.: 215,949

[22] Filed: Dec. 12, 1980

Related U.S. Application Data

[63] Continuation of Ser. No. 30,398, Apr. 16, 1979, abandoned.

[51] Int. Cl.³ .............................................. A61M 5/00
[52] U.S. Cl. .................................. 128/214 E; 128/274
[58] Field of Search ........... 128/214 R, 214 E, 214 F, 128/274; 137/496, 511

[56] References Cited

U.S. PATENT DOCUMENTS

| | | | |
|---|---|---|---|
| 2,538,662 | 1/1951 | Abbott | 128/214 |
| 2,999,499 | 9/1961 | Willett | 128/214 |
| 3,886,937 | 6/1975 | Bobo et al. | 128/214 |
| 3,976,402 | 8/1976 | Lundquist | 128/214 E |
| 3,978,857 | 9/1976 | McPhee | 128/214 |
| 4,005,710 | 2/1977 | Zeddies et al. | 128/214 |
| 4,034,754 | 7/1977 | Virag | 128/214 R |
| 4,141,379 | 2/1979 | Manske | 128/214 G |

Primary Examiner—Richard J. Apley
Assistant Examiner—T. J. Wallen
Attorney, Agent, or Firm—Roger A. Williams

[57] ABSTRACT

An administration set with a check valve above a side port where the side port is used for the introduction of a secondary liquid, and this check valve is extremely sensitive to minute pressure changes in the combined administration set. The valve includes a very light disk supported on a series of upstanding prongs that hold a sealing surface of the disk to within 0.002 to 0.030 inch of a valve seat when in open position. The highly sensitive valve is easy to manufacture, easy to prime, and resists malfunctioning due to sticking shut or open. The valve also permits high flow rates (up to 500 ml/hr. or more) commonly used in medical administration sets.

14 Claims, 3 Drawing Figures

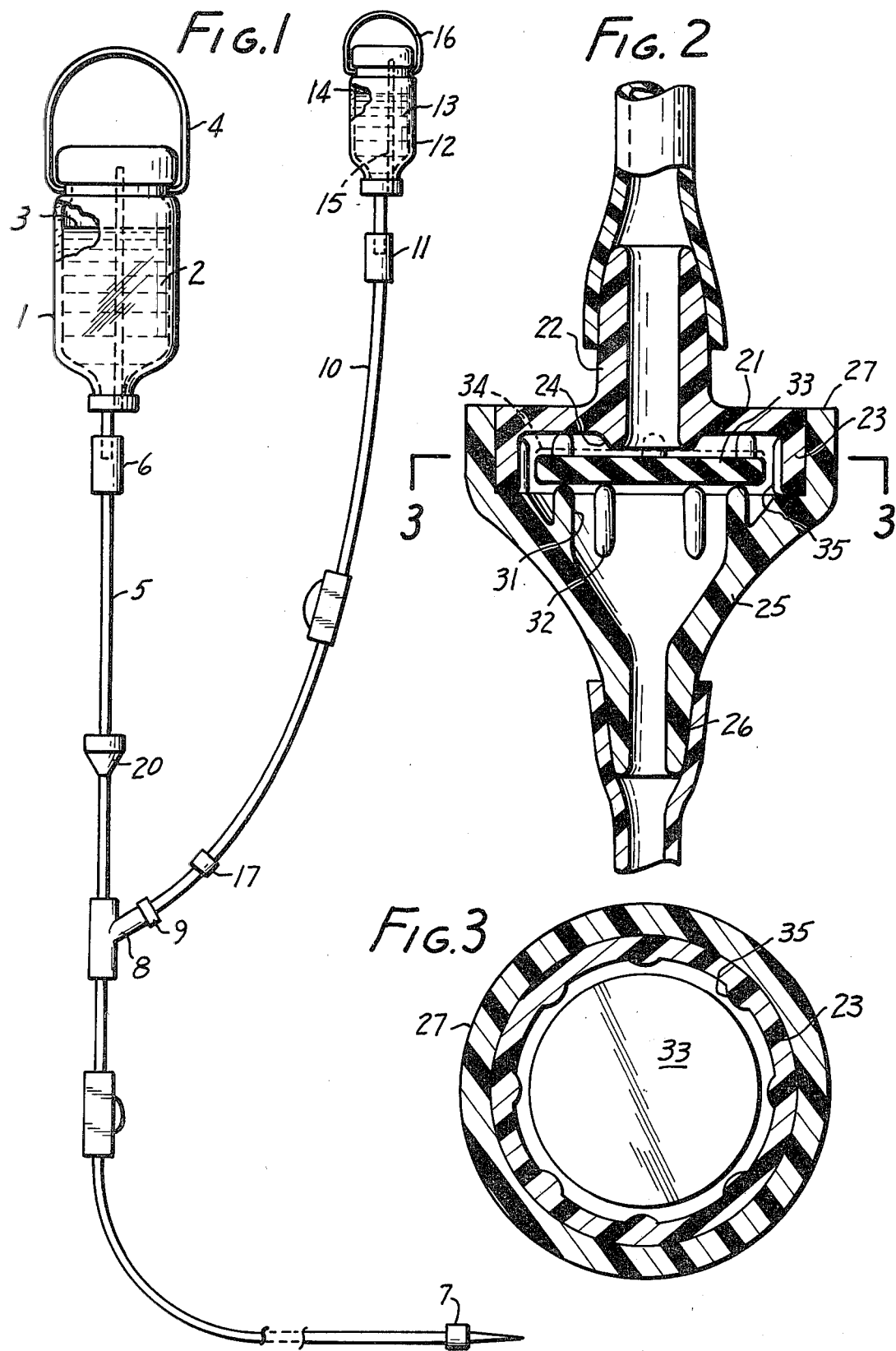

MEDICAL ADMINISTRATION SET WITH BACKFLOW CHECK VALVE

This application is a continuation of application Ser. No. 030,398, filed Apr. 16, 1979, now abandoned.

BACKGROUND

It has been known to administer plural medical liquids through a tubular set that is generally in the form of a Y. U.S. Pat. Nos. 3,886,937 and 4,034,754 describe duckbill check valves in one arm of the Y set upstream of the crotch of the Y, sometimes called a side port, for a secondary liquid source. As shown in U.S. Pat. No. 4,034,754, the secondary liquid container on the right is placed slightly higher than the primary liquid container on the left. Very slight pressure changes in the Y set caused by changing liquid levels opens and closes the check valve to sequentially administer the tube liquids.

While the concept is known to use a backflow check valve in such administration set, there have been problems in leakage and sensitivity. The duckbill type valves as described in U.S. Pat. No. 3,886,937 and 4,034,754 have experienced problems in sticking closed or not completely shutting off; i.e., liquid will still bleed to the primary container when the check valve should be closed.

A preloaded disk valve which is distortably urged against a valve seat is also described in U.S. Pat. No. 3,886,937. However, such preloaded valve has sluggish response in that a relatively large differential head pressure is needed in the primary container to open such valve. Also, it is difficult in manufacturing to accurately control the precise preloading necessary so the valve is not overloaded or underloaded.

A specially molded valve member with depending feet structure is described in U.S. Pat. No. 4,005,710. This valve requires an expensive molding process to get its unique shape. In addition, its large cylindrical side surface, which includes an outer surface of the legs, sometimes tends to cling to the vertical housing wall causing the valve member to stick in either the open or closed position. It must be recognized that the pressure differential between the two liquid containers might be as small as 2 inches of water and this is not sufficient to refloat the valve member stuck to the side wall of the housing by liquid surface tension.

Other background prior art includes U.S. Pat. Nos. 2,999,499 and 2,538,552, which again includes massive molded movable valve members of a special T-shape. Such valves, as shown in U.S. Pat. No. 2,999,499, may be adequate for response to extremely high pressure injections from a piston type syringe, but again would be sluggish in response to minute changes in head pressure between two gravity feed containers.

In addition to the problem caused by very low pressure differentials in medical liquid administration sets, the flow rates vary over a wide range up to 500 ml/hr. or more. It has previously been thought necessary to provide wide throated valves with large passages to handle this high flow rate in an administration set.

SUMMARY OF THE INVENTION

The present invention overcomes the problems explained above relating to administration set check valves. The applicant has unexpectedly found that a very small gap (0.002 to 0.030 inch) between a sealing surface of a compliant valve member having sufficient width is capable of handling fast flow rates commonly used with medical administration sets, while still opening and closing with the minute pressure differential of 2 inches of water. Preferably, the valve member is a rubber disk having a width at least 5 times greater than its thickness.

THE DRAWINGS

FIG. 1 is a side elevational view of the administration set after its side port has been connected to a secondary liquid source;

FIG. 2 is an enlarged sectional view of the backflow check valve structure; and

FIG. 3 is a sectional view taken along line 3—3 of FIG. 2.

DETAILED DESCRIPTION

FIG. 1 shows a primary medical liquid bottle 1 containing a liquid 2 that has an upper surface 3. Container 1 can be a bottle with an integral hanger 4.

The administration set includes a tubular conduit 5 having a drip chamber 6 with a spike at its upper end for coupling with an outlet port of container 1. A lower end of the administration set has a needle 7, such as for inserting into a patient's vein. Intermediate of the two ends of the administration set is a side port 8 which is shown here in the form of a Y-shaped connector with a puncturable resealable diaphragm 9. A check valve 20 is located between the side port 8 and drip chamber 6. The administration set as described so far can be sold as a separate unit.

When it is desired to connect the administration set with its side port 8 into a "Y-set" construction, a secondary conduit 10 is connected at a drip chamber 11 to a secondary container 12 with a spike. Liquid 13 in this secondary container has an upper surface 14. For purpose of illustration, secondary container 12 has been shown as a glass bottle with an air inletting tube 15 and a hanging bail 16. However, it is understood that other types of secondary containers, such as collapsible thermoplastic bottles, collapsible bags, rigid bottles with other types of air inletting systems, etc., could be used with the present administration set. Such types of container could also be used for the primary container.

A lower needle 17 of the secondary conduit 10 is attached to the side port as shown in FIG. 1. With liquid level 14 in the secondary container being higher than liquid level 3 in the primary container, there is a pressure differential on check valve 20 tending to close it until the level of the secondary liquid falls below the level 3 of the primary container, at which time valve 20 will open and primary liquid will be administered to the patient.

The overall description of such backflow check valve functioning has been described in the prior art. However, the problems with such check valves have included the complex shapes of a movable valve member in a housing, startup, sticking and leakage problems with duckbill type valves, and sluggish or nonsensitive response to slight pressure changes between the liquid in the two containers. The pressures exerted on the valve are in the order of 0 to 10 inches of water and the flow rates normally vary from 1 to 500 ml/hr., but sometimes can be higher. For sensitive response, it is desirable to have a valve that can open and close with very small pressure differentials, often 1-2 inches of water.

FIG. 2 shows the internal working structure of a very sensitive check valve in an administration set, and the check valve is simple to manufacture. Here an upper housing member 21 has a tubular adapter 22 and a skirt 23. A valve seat 24 surrounds an inlet of upper housing member 21.

A lower housing member 25 has a tubular adapter 26 and an upstanding skirt 27 that telescopically receives the upper housing member 21. Various types of seals and skirt structure could be used to form the housing.

Lower portion 25 of the housing includes a series of 3 to 12 upstanding prongs, such as 31 and 32, with rounded upper ends. These prongs are very closely spaced relative to the valve seat 24 and support a thin rubber disk 33 when the valve is in open position. This disk could be made of any compliant material, such as rubber. The disk has a thickness of from 0.010 to 0.040 inch and its width is at least 5 times greater than its thickness. The dotted line showing at 34 indicates the upper position of the disk 33 at the shut-off position of the valve. Preferably, this distance is from 0.002 to 0.030 inch, and the applicant has found that such very close positioning of disk 33 does not interfere with output flow volumes from the primary container.

The rounded tips of prongs 31 and 32 reduce the area of contact between the prongs and disk 33 to less than 20% of the disk's bottom surface area. The upper and lower surfaces of disk 33 are generally flat. The small contact area between the prongs and the disk, as well as a series of vertical ribs 35 on the housing, prevents the disk 33 from hanging up or sticking to the housing. Instead, it is extremely sensitive to small pressure changes in the administration set. It has also been found that the valve is operable in all orientations and can even work upside down.

In the foregoing description, a specific example has been used to describe the invention. However, it is understood by those skilled in the art that certain modifications can be made to this example without departing from the spirit and scope of the invention.

I claim:

1. A medical administration set with a check valve, wherein the improvement comprises: a valve housing having a valve seat; a compliant sheet-like valve member being free of mechanical bias against the valve seat and movably confined in a compartment of the housing without a physical anchoring to the housing; and a plurality of spaced supports connected to the housing which maintain a sealing surface of the valve member at a distance of 0.002 to 0.030 inch from the valve seat when the valve is open; said valve member having sufficient width to cause a pressure differential in either direction across the valve member as low as 2 inches of water to alternately open and close the valve by means of gravity liquid draining at liquid flow rates commonly used in medical administration sets.

2. A medical administration set as set forth in claim 1, wherein the valve is capable of handling up to at least 500 ml/hr. of liquid.

3. A medical administration set as set forth in claim 1, wherein the valve is a disk having a width at least 5 times greater than its thickness.

4. A medical administration set as set forth in claim 3, wherein the disk is a flat sheet having generally parallel upper and lower surfaces.

5. A medical administration set as set forth in claim 1, wherein the supports contact less than 20% of the area of the valve's surface facing the supports.

6. A medical administration set as set forth in claim 1, wherein the supports include a series of 3-12 prongs.

7. A medical administration set as set forth in claim 1, wherein the housing has a side wall with means to prevent the valve member from sticking to such side wall.

8. A medical administration set as set forth in claim 7, wherein the means includes a series of ribs circumferentially spaced about the side wall.

9. A medical liquid check valve, wherein the improvement comprises: a valve housing with a valve seat; a compliant sheet-like valve member being free of mechanical bias against the valve seat and movably confined within a compartment of the housing without physical anchoring to the housing; and a plurality of spaced supports connected to the housing which maintains a sealing surface of the valve at a distance of 0.002 to 0.030 inch from the valve seat when the valve is open; said valve member having a sufficient width to cause a pressure differential in either direction across the valve member as low as 2 inches of water to alternately open and close the valve by means of gravity liquid draining at liquid flow rates commonly used in medical administration sets.

10. A medical liquid check valve as set forth in claim 9, wherein the valve is capable of handling up to at least 500 ml/hr. of liquid.

11. A medical liquid check valve with a housing having an internal valve seat and a movable valve member movably confined within a compartment of the housing without a physical anchoring to the housing for maintaining a sealing surface of the valve member at a distance of 0.002 to 0.030 inch of the valve seat when the valve is open; said valve member being of a compliant sheet-like construction and being free of mechanical bias against the valve seat; said valve member having a sufficient width to cause a pressure differential in either direction across the valve member as low as 2 inches of water to alternately open and close the valve by means of gravity liquid draining at liquid flow rates commonly used in medical liquid administration sets.

12. A medical liquid check valve as set forth in claim 11, wherein the valve is capable of handling up to at least 500 ml/hr. of liquid.

13. A medical liquid check valve as set forth in claim 11, wherein the valve member is a resilient disk having a width at least 5 times greater than its thickness.

14. A medical liquid check valve as set forth in claim 11, wherein the valve functions in all physical orientations.

* * * * *

REEXAMINATION CERTIFICATE (387th)
United States Patent [19]
McPhee

[11] B1 4,354,492
[45] Certificate Issued Sep. 10, 1985

[54] MEDICAL ADMINISTRATION SET WITH BACKFLOW CHECK VALVE

[75] Inventor: Charles J. McPhee, Huntington Beach, Calif.

[73] Assignee: American Hospital Supply Corporation, Evanston, Ill.

Reexamination Request:
No. 90/000,532, Mar. 20, 1984

Reexamination Certificate for:
Patent No.: 4,354,492
Issued: Oct. 19, 1982
Appl. No.: 215,949
Filed: Dec. 12, 1980

Related U.S. Application Data

[63] Continuation of Ser. No. 30,398, Apr. 16, 1979, abandoned.

[51] Int. Cl.$^3$ .............................................. A61M 5/00
[52] U.S. Cl. ................................ 604/247; 137/528; 604/81
[58] Field of Search ............................ 604/247, 81, 9

[56] References Cited
U.S. PATENT DOCUMENTS

| | | | |
|---|---|---|---|
| 605,549 | 11/1898 | Johansson | 137/843 |
| 1,251,758 | 1/1918 | Dayton | 137/843 |
| 1,269,616 | 6/1918 | Bozec | 137/533.19 |
| 1,576,128 | 3/1926 | Ballard | 604/213 |
| 2,497,906 | 2/1950 | Peters et al. | 137/496 |
| 2,538,662 | 1/1951 | Abbott | 128/214 |
| 2,919,670 | 1/1960 | Clark, Jr. et al. | 137/533 |
| 3,109,444 | 11/1963 | McKee | 137/533.17 |
| 3,233,610 | 2/1966 | Wade | 128/350 |
| 3,521,635 | 7/1970 | Koehn | 604/254 |
| 3,550,616 | 12/1970 | Graham et al. | 137/533.19 |
| 3,889,710 | 6/1975 | Brost | 137/843 |
| 3,978,857 | 9/1976 | McPhee | 604/257 |
| 4,005,710 | 2/1977 | Zeddies et al. | 137/533 |
| 4,141,379 | 2/1979 | Manske | 137/496 |

*Primary Examiner*—C. Fred Rosenbaum
*Assistant Examiner*—Michelle Lester
*Attorney, Agent, or Firm*—John A. Kane

[57] ABSTRACT

An administration set with a check valve above a side port where the side port is used for the introduction of a secondary liquid, and this check valve is extremely sensitive to minute pressure changes in the combined administration set. The valve includes a very light disk supported on a series of upstanding prongs that hold a sealing surface of the disk to within 0.002 to 0.030 inch of a valve seat when in open position. The highly sensitive valve is easy to manufacture, easy to prime, and resists malfunctioning due to sticking shut or open. The valve also permits high flow rates (up to 500 ml/hr. or more) commonly used in medical administration sets.

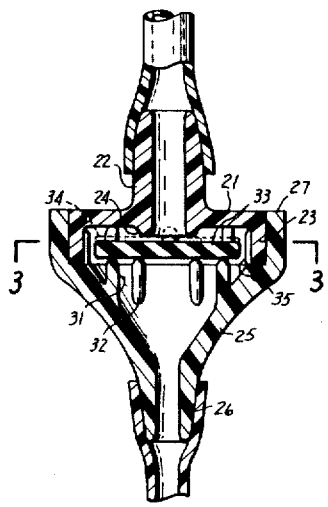

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4–6 and 8 is confirmed.

Claims 1–3, 7, and 9–14 are cancelled.

New claim 15 is added and determined to be patentable.

15. *A medical administration set as set forth in claim 1, wherein the valve member is a disk comprising a flat sheet having generally parallel upper and lower surfaces.*

* * * * *